US009109991B2

(12) United States Patent
Yang et al.

(10) Patent No.: US 9,109,991 B2
(45) Date of Patent: Aug. 18, 2015

(54) ELECTROCHEMICAL PROBE WITH COATED, FINGERED ELECTRODES FOR CORROSION MONITORING IN OIL-WATER MIXTURES AND GAS SYSTEMS CONTAINING HYDROGEN SULFIDE

(71) Applicants: Lietai Yang, San Antonio, TX (US); Xiaodong Sun Yang, San Antonio, TX (US)

(72) Inventors: Lietai Yang, San Antonio, TX (US); Xiaodong Sun Yang, San Antonio, TX (US)

( * ) Notice: Subject to any disclaimer, the term of this patent is extended or adjusted under 35 U.S.C. 154(b) by 48 days.

(21) Appl. No.: 13/873,222

(22) Filed: Apr. 30, 2013

(65) Prior Publication Data
US 2014/0318959 A1 Oct. 30, 2014

(51) Int. Cl.
*G01N 17/04* (2006.01)
(52) U.S. Cl.
CPC ........... *G01N 17/04* (2013.01); *Y10T 29/49224* (2015.01)
(58) Field of Classification Search
CPC ... G01N 17/006; G01N 17/008; G01N 17/02; G01N 17/04–17/046
USPC ....................................... 204/404; 205/775.5
See application file for complete search history.

(56) References Cited

U.S. PATENT DOCUMENTS

| | | | |
|---|---|---|---|
| 4,752,360 A * | 6/1988 | Jasinski | ..................... 205/776.5 |
| 6,132,593 A | 10/2000 | Tan | |
| 6,683,463 B2 | 1/2004 | Yang et al. | |
| 6,805,788 B1 * | 10/2004 | Gonzalez-Martin et al. | .......................... 205/775.5 |
| 7,180,309 B1 | 2/2007 | Yang | |
| 8,298,390 B2 | 10/2012 | Yang et al. | |
| 2010/0126859 A1 * | 5/2010 | Yang et al. | ..................... 204/404 |

OTHER PUBLICATIONS

S. Papavinasam, "Electroch.Tech. for Corrosion Monitoring", in "Corrosion Monitoring Techniques," Lietai Yang, ed., Woodhead Publishing, Cambridge, UK (2008), pp. 77-79.
L. Yang, et al., "Real-Time Monitoring of Carbon Steel Corrosion in Crude Oil and Salt Water Mixtures Using Coupled Multielectrode Sensors," Corrosion/2005, paper No. 05293.
[Continued from above] (Houston, TX: NACE International, 2005).
N. Sridhar, L. Yang and F. Song "Application of Multielectrode Array to Study Dewpoint Corrosion in High Pressure Natural Gas Pipeline Environments", Corrosion/2006, paper.
[Continued from above] paper No. 06673 (Houston, TX: NACE, 2006).

* cited by examiner

*Primary Examiner* — J. Christopher Ball

(57) ABSTRACT

Electrochemical probes for corrosion monitoring in an environment that may cause the formation of electron conducting deposits and the method for making such probes were disclosed. The probes have exposed fingered electrodes. Except for the sensing areas at the tip sections, all surfaces of the exposed electrodes are coated with an inner electrically insulating coating or tubing and one or more additional coating(s) or tube(s). One of the additional coatings is ion conducting. The electrodes are spaced such that there are gaps between the outer surfaces of the neighboring electrodes to prevent the formation of a continuously distributed electron conducting deposits between the sensing surface of one electrode and the sensing surfaces of the other electrodes. These probes are especially suitable for applications in gas systems and oil-water mixtures containing hydrogen sulphide ($H_2S$).

19 Claims, 8 Drawing Sheets

US 9,109,991 B2

ELECTROCHEMICAL PROBE WITH COATED, FINGERED ELECTRODES FOR CORROSION MONITORING IN OIL-WATER MIXTURES AND GAS SYSTEMS CONTAINING HYDROGEN SULFIDE

TECHNICAL FIELD OF THE INVENTION

This invention relates to electrochemical probes for corrosion monitoring in oil-water mixtures and gas systems containing hydrogen sulfide that causes the formation of electron conducting deposits on the sensing electrodes and leads to the short-circuiting among neighboring electrodes.

BACKGROUND OF THE INVENTION

Coupled multielectrode array sensors (CMAS) (see U.S. Pat. No. 6,683,463, U.S. Pat. No. 6,132,593, and U.S. Pat. No. 7,180,309) and other electrochemical sensors for corrosion monitoring are subject to the bridging effect of the formation of electron conducting deposits that causes the short-circuiting among the sensing electrodes [see S. Papavinasam, "Electrochemical Techniques for Corrosion Monitoring," in "Corrosion Monitoring Techniques," Lietai Yang, ed., Woodhead Publishing, Cambridge, UK (2008), pages 77-79]. These electron conducting deposits may be formed by the corrosion of iron in an environment containing hydrogen sulfide ($H_2S$), because the corrosion products (such as FeS) are semiconductor materials. When the sensing electrodes are short-circuited, the corrosion current cannot be accurately derived by the current that is measured by the sensor instrument. Thus, the sensor instrument cannot effectively measure the corrosion rate. A CMAS probe with coated, fingered electrodes has been described for use in liquid systems containing hydrogen sulfide to avoid the bridging among the neighboring electrodes (see U.S. Pat. No. 8,298,390). In the probe with coated, fingered electrodes, the active sensing surface area of each electrode is physically separated from the sensing areas of neighboring electrodes by a long, coated surface. Such a long, coated surface makes it difficult to form a continuous layer of an electron conducting path among neighboring electrodes' sensing areas. However, such probes cannot be used in a system that cannot form an ion conducting path among the neighboring electrodes' sensing areas. Examples of such systems are untreated natural gases and oil-water mixtures that contain hydrogen sulphide. CMAS probes with closely packed electrodes on a small surface area have been used in oil-water mixtures (see Yang, et al 2005) and simulated natural gas systems (see Sridhar et al, 2006) that did not contain hydrogen sulphide. In the CMAS probes with closely packed electrodes on a small surface area, the sensing area of one electrode is close to the sensing areas of the neighboring electrodes and the ion conducting path can be easily formed by a layer of water adsorbed on the surface between the sensing area of one electrode and the sensing areas of other electrodes. This is in the case of natural gas when the humidity is above a certain point that would cause corrosion. The ion conducting path can also be easily formed by small sized water particulates in the case of oil-water mixtures. However, the probe surface where the sensing areas are can be easily covered by a layer of electron conducting deposits and such a closely packed CMAS probe is subject to the bridging effect.

This invention is related to a CMAS probe that has coated, fingered electrodes and has a mechanism to maintain the ion conducting path among the active sensing areas of the electrodes that are physically separated to avoid the formation of a continuous layer of electron conducting deposits along the path between any pairs of the electrodes.

Figure 1:
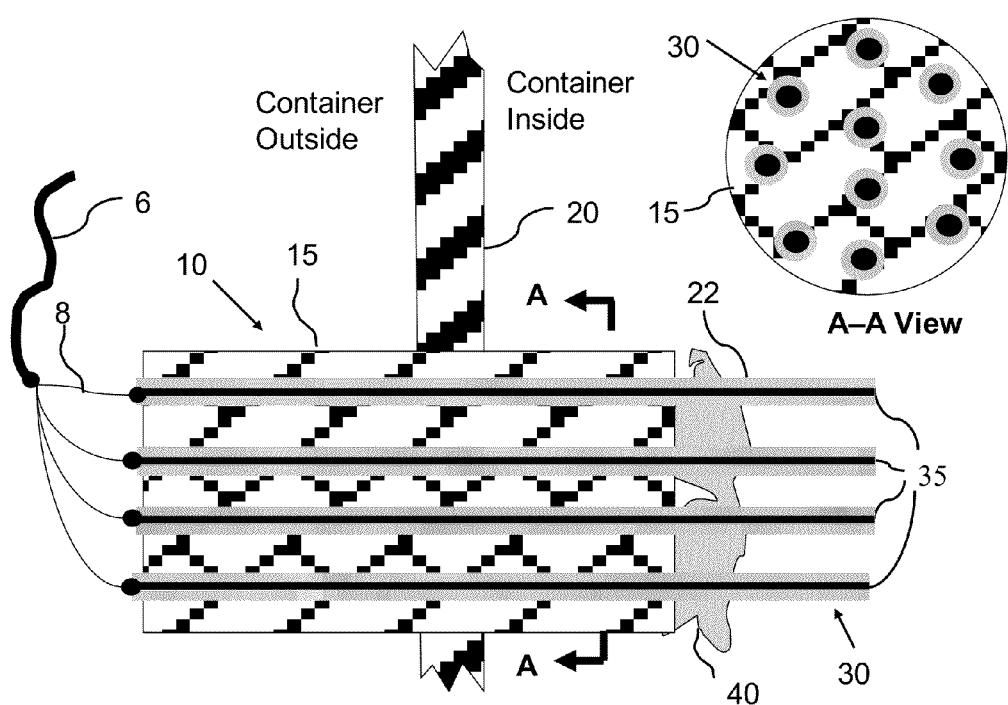
FIG. 1 illustrates a typical prior art coupled multielectrode array sensor (CMAS) probe with coated, fingered electrodes to avoid the short-circuiting by electron conducting deposits among the electrodes' sensing areas.

REFERENCE NUMBERS OF DRAWINGS 5 insulation material (usually epoxy or ceramic)
6 probe cable
8 electrical leads connected to electrodes (see 30 below)
10 probe
15 probe body
20 container wall (corrosive medium, including electron conducting materials, is inside the container)
22 insulating coating or tubing
23 thin insulating coating or tubing that defines the active sensing surface area of each electrode (or called sensing area of each electrode)
25 ion conducting coating or tubing that maintains ion conducting paths among the sensing areas of the electrodes
27 ion conducting material at probe body base that ensures ion conducting paths among the ion conducting coatings or tubings on different electrodes
28 packing of a conducting material at probe body base that ensures ion conducting paths among the ion conducting coatings or tubings on different electrodes
29 coating (or tubing) that is resistant to the formation of corrosion products on its surface
30 electrodes covered by coating or tubing (called coated electrodes)

31 uncoated electrode
35 sensing areas of electrodes
40 solid deposits that may be electron conducting

PRIOR ARTS

FIG. 1 shows a prior art CMAS probe (10) that has coated, fingered electrodes to avoid the formation of electron conducting deposits along the path from the sensing area of one electrode to the sensing areas of the other electrodes. In this design, the electrodes (30) are coated with (or covered by) an electrically insulating coating (or a plastic tubing) (22) and embedded in the probe body (15). The coated electrodes (30) are connected to the electrical cable (6) by the electrical leads (8). The coating (22) on the side surface of the coated electrode can be made of an epoxy, polytetrafluoroethylene (PTFE) tube, polyetheretherketone (PEEK) tube, or other polymer tube or paint that is resistant to the formation of corrosion product deposits (40) that may be electron conducting. The electron conducting solid deposits often form at the sensing areas (35) of the electrodes, if the probe is mounted to a container (20) that contains hydrogen sulfide. Unlike the surface of a corroded metal, which allows the easy attachment and build-up of corrosion product deposits (40), the coating surface is resistant to the attachment of the electron conducting deposits so that the deposits cannot easily grow on the coating surfaces. In addition the sensing areas are far away from each other and it is difficult to form continuous electron conducting deposits that allow the electrons to travel from the sensing area (35) of one electrode to the sensing areas (35) of one or more other electrodes.

FIG. 1 is suitable for corrosion monitoring in systems containing a liquid electrolyte which provides the ion conducting path among the electrodes. However, FIG. 1 is not suitable for use in a gas system or an oil-water mixture because of the absence of an ion conducting medium between the sensing areas (35) of the coated electrodes (30).

DETAILED DESCRIPTIONS OF THE INVENTION

FIG. 2

Figure 2:
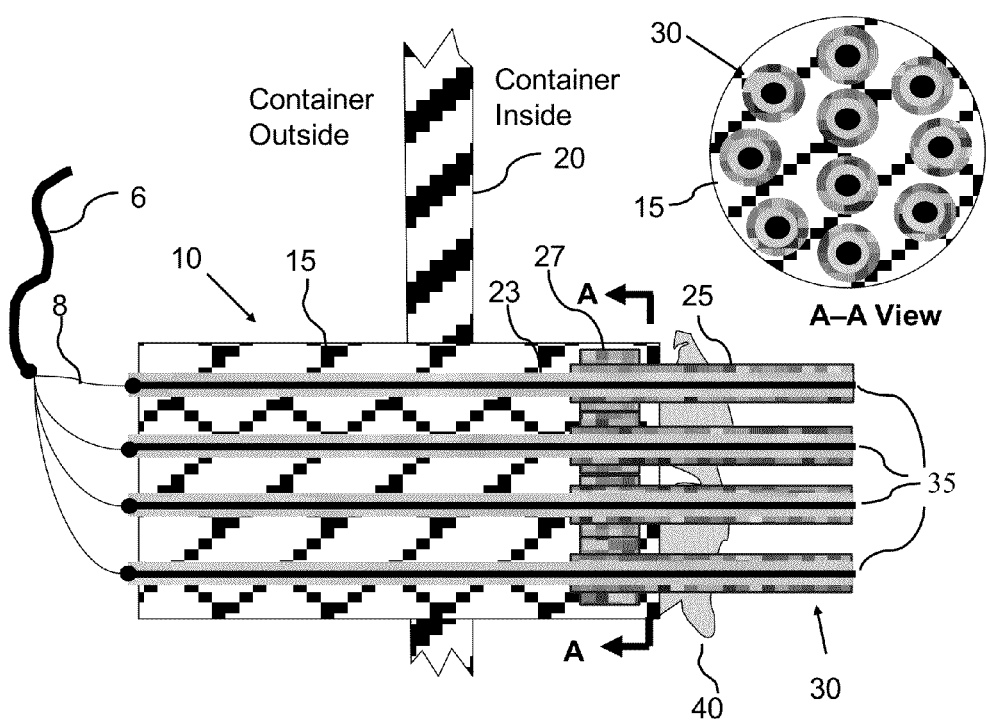
FIG. 2 illustrates a CMAS probe with fingered electrodes coated with double layers to minimize the possibility of forming electron conducting paths by corrosion deposits and to maintain ion conducting paths among the electrodes' sensing areas.

FIG. 2 illustrates a CMAS probe with fingered electrodes coated with double layers to minimize the possibility of forming an electron conducting path by corrosion deposits and to maintain an ion conducting path between the sensing area of one electrode and the sensing areas of other electrodes in the absence of a liquid electrolyte. In FIG. 2, the insulating coating (22) of FIG. 1 is changed to a thin insulating coating or tubing (23) as the first layer of coating and a second layer of coating or tubing (25) that is hygroscopic and becomes ion conducting in a corrosive environment is added to the outside of the thin, insulating coating (23). Additional ion conducting material (27) may be added at the base of the probe body so that the surfaces of the ion conducting coating or tubing (25) on all electrodes of the CMAS probe are interconnected by the additional ion conducting material. Similarly in FIG. 1, the sensing areas of the electrodes are far away from each other. The embodiment of FIG. 2 also prevents the formation of continuous electron conducting deposits that cause electrons to travel from the sensing area (35) of one coated electrode to the sensing area(s) (35) of one or more other coated electrode(s) (30).

Electrochemical corrosion of a metal only occurs when an electrolyte is present on the metal surface. In the case of the electrochemical corrosion in a gas system, the relative humidity of the gas system must be higher than a critical relative humidity so that a layer of water film can be formed on the metal surface to cause the metal to corrode. In the case of the electrochemical corrosion in an oil-water mixture, liquid water or liquid water particulate must be in contact with the metal surface to cause the metal to corrode. Because the ion conducting coating or tubing is hygroscopic, it absorbs water and becomes ion conducting from the gas phase when its relative humidity is such that it causes corrosion or from the oil-water mixture when water is present in the mixture.

As the thickness of the electrically insulating coating or tubing (23) is thin (usually 0.01 to 0.3 mm), layers of electrolyte can be relatively easily formed between the ion conducting coating (25) and the sensing area of the electrode (35) [across the thin ring section of the insulating coating or tubing (23)] in the gas phase when the relative humidity is such that it causes metal corrosion. Layers of electrolyte can also be formed in an oil-water mixture, especially when the surface of the thin cross section of the coating (23) is rough or when it is covered by dust or other solid deposits. Therefore, ion conducting paths are present between the sensing area of one electrode and the sensing areas of other electrodes when the probe is in a gas system or a mixture of crude oil and water that would cause the metal to corrode.

The thin electrical insulation coating or tubing (23) provides mainly two functions. One such function is that it prevents any direct contact between the ion conducting material (25) and the metal electrode (35) because such direct contact would cause the corrosion of the metal electrode by the ionic coating and affect the corrosion signal from each electrode. The other function is that the thin insulating coating limits the corrosion reaction to a well defined sensing surface area exposed at the end of each electrode (called sensing area) so that the corrosion current can be accurately converted to corrosion current density for calculating the corrosion rate.

Figure 3:
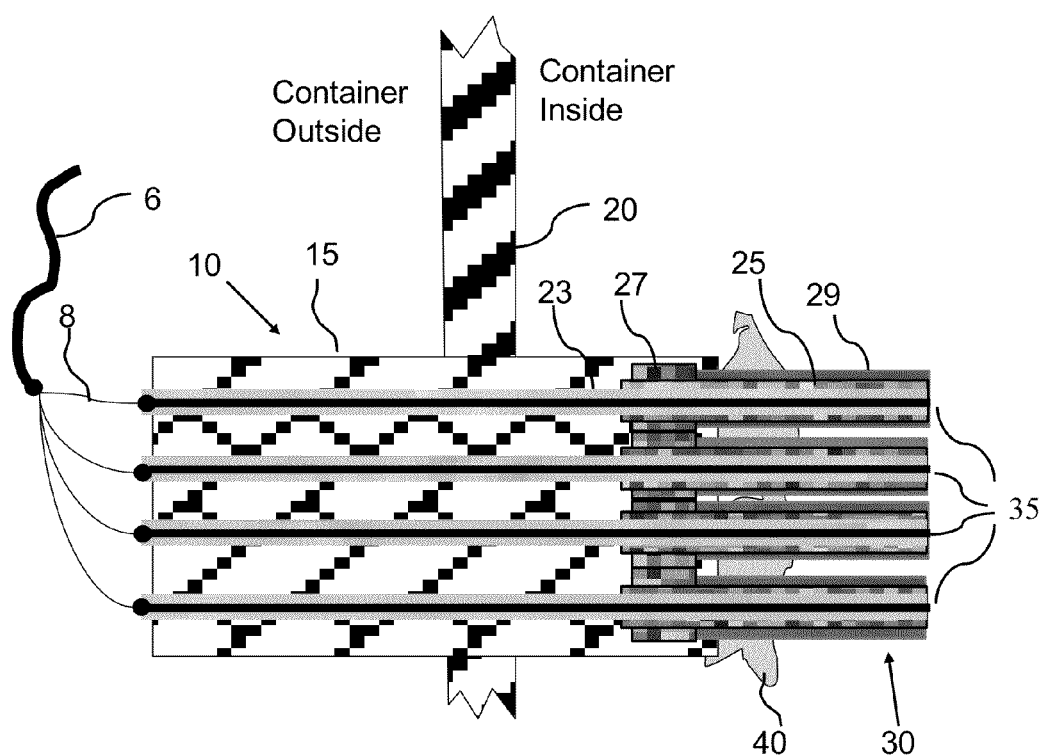
FIG. 3 illustrates a CMAS probe with fingered electrodes coated with triple layers to minimize the possibility of forming electron conducting paths by corrosion deposits and to maintain ion conducting paths among the electrodes' sensing areas.
Figure 4:
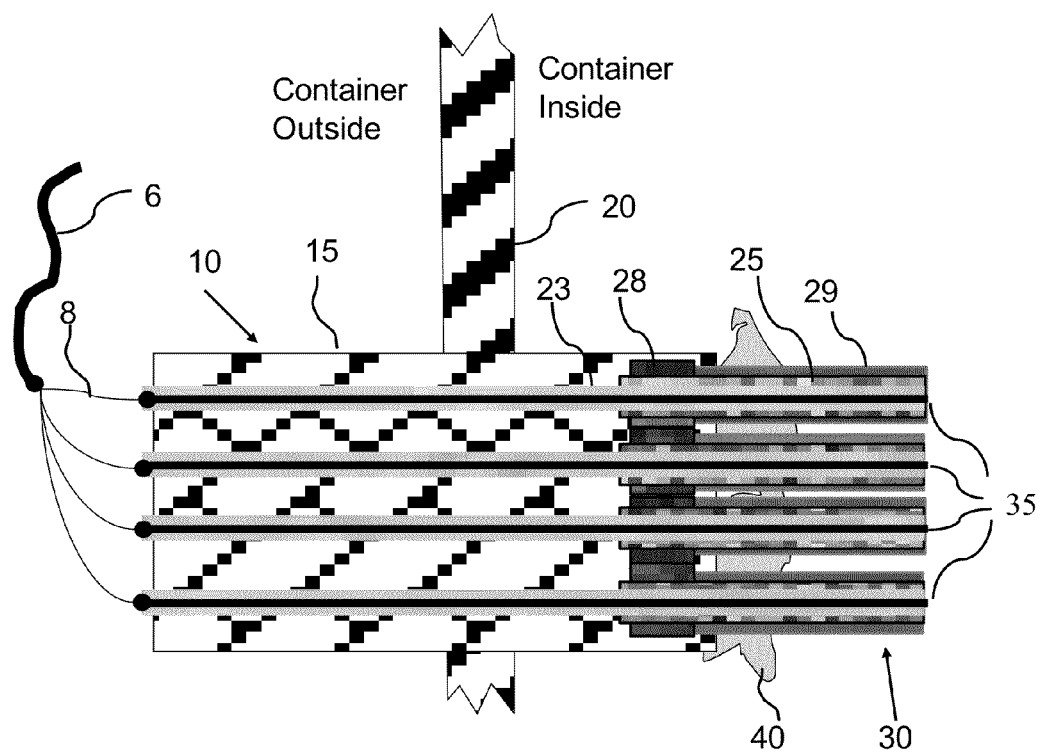
FIG. 4 illustrates a CMAS probe with fingered electrodes coated with triple layers and filled with a different ion conducting packing among neighboring electrodes.

FIGS. 3 and 4

FIG. 3 illustrates a CMAS probe with fingered electrodes coated with triple layers to minimize the possibility of forming an electron conducting path by corrosion product deposits and to maintain an ion conducting path between the sensing area of one electrode and the sensing areas of the other electrodes. In FIG. 3, a third layer of coating or tubing (29) is applied over the top of the ion conducting coating (25). The third layer of the coating does not need to be ion conductive and it is easier to find a non-ion conducting material that has a good resistance to the attachment of the electron conducting deposits so that the deposits cannot easily grow on the coated electrode (30).

The other functions of the third layer of the coating include mechanical protection of the ionic coating and retaining the water content absorbed by the ion conducting coating when the water content in the gas system varies.

FIG. 4 illustrates a CMAS probe with fingered electrodes coated with triple layers and filled with anion conducting packing material (28) that is different from the ion conducting coating (25) between neighboring electrodes. The ion, conducting coating can be of any material that is conductive under the conditions that support corrosion. An example of such packing materials is porous ceramic soaked with a sodium chloride solution. In a dry gas, no corrosion will occur on the sensing electrode (35) and the sodium chloride will form fine crystals which are not conductive. When the humidity in the gas increases to a value that supports corrosion (for example, above 75%), the chloride salt crystal inside the porous packing will deliquescence and the porous ceramic will be ion conducting. Thus, it is electrically connecting the surfaces of the ion conducting coatings on all of the electrodes (35).

FIG. 5

Figure 5:
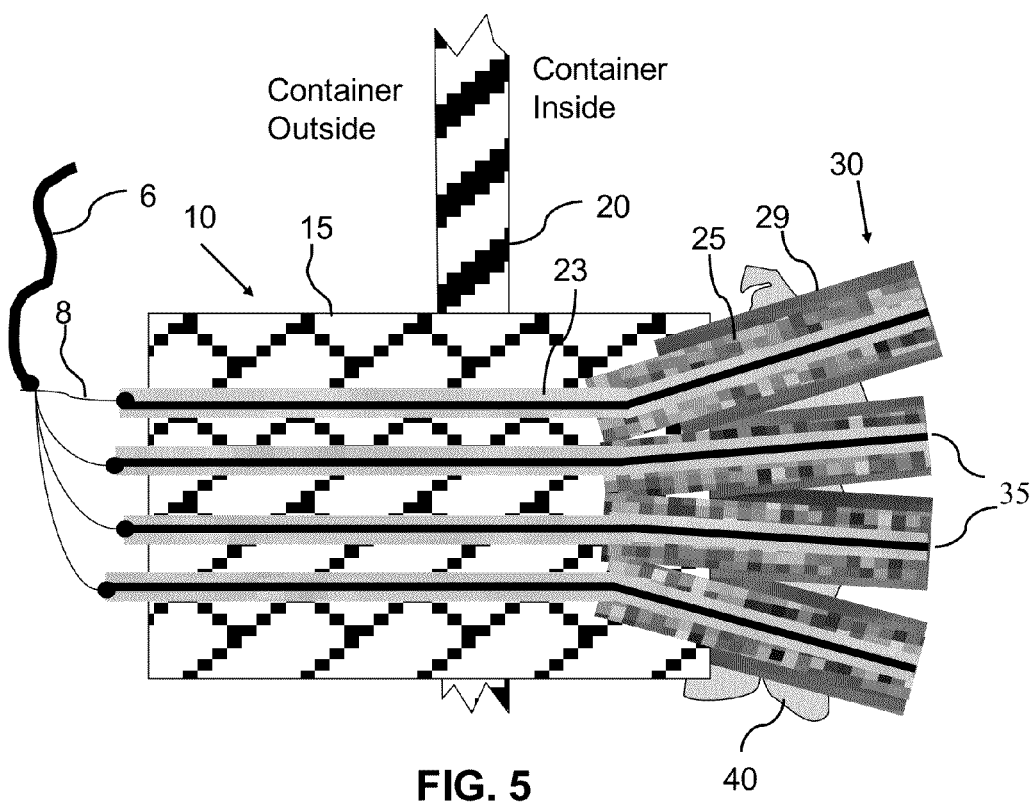
FIG. 5 illustrates a CMAS probe with coated fingered electrodes that are bent away to further increase the distance among the electrodes to avoid the short-circuiting among the electrodes' sensing areas by electron conducting deposits.

FIG. 5 illustrates a CMAS probe with coated, fingered electrodes that are bent to further increase the distance among the sensing areas of the electrodes.

Figure 6:
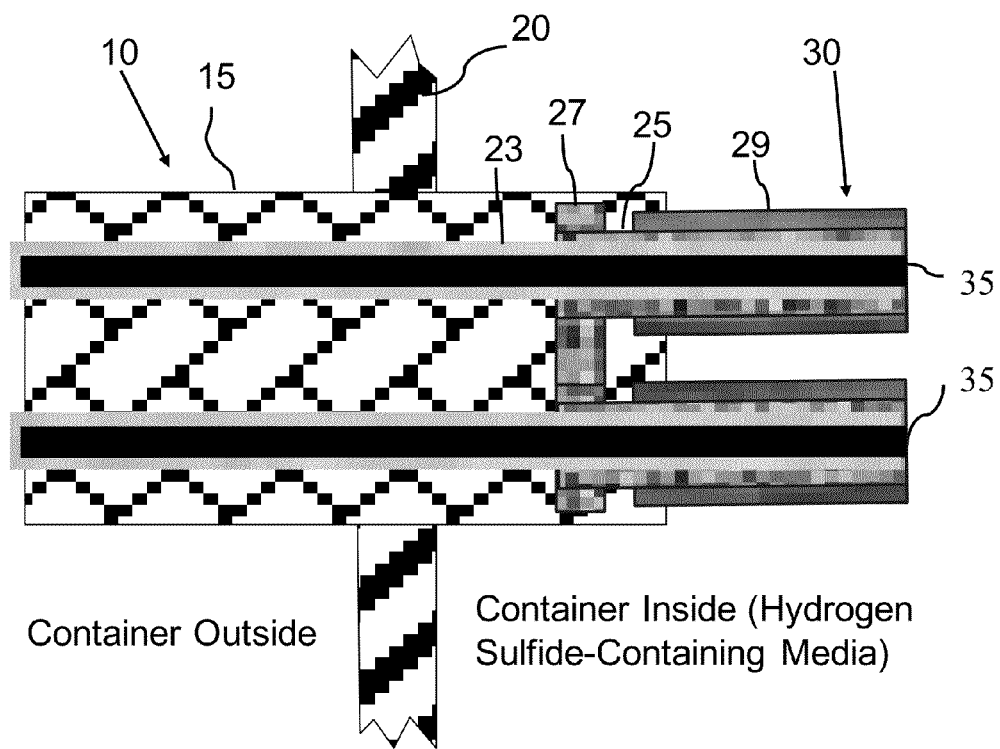
FIG. 6 illustrates an electrochemical probe with two fingered electrodes coated with triple layers to minimize the possibility of forming an electron conducting path by corrosion deposits and to maintain an ion conducting path between the two electrodes' sensing areas.
Figure 7:
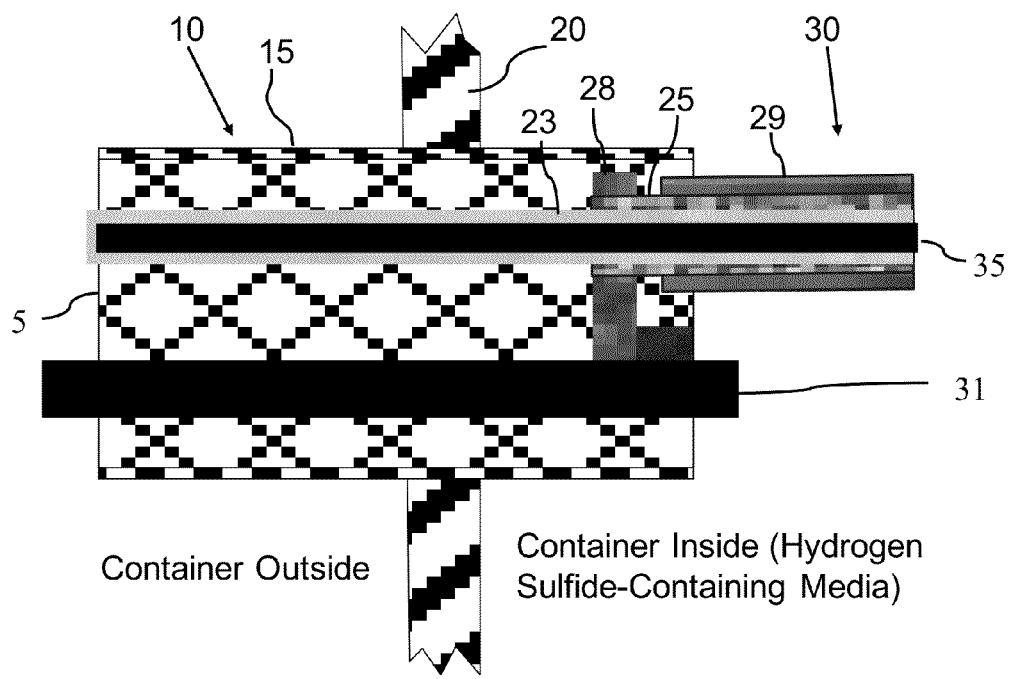
FIG. 7 illustrates an electrochemical probe with one fingered electrode coated with triple layers to minimize the possibility of forming an electron conducting path by corrosion deposits and to maintain an ion conducting path between the electrode sensing area and the surface of an uncoated electrode.

FIGS. 6 and 7

The concept of using multilayer coated fingered electrodes, so that it is resistant to the formation of continuous electron conducting deposits to minimize the bridging effect in hydrogen sulfide environments without the presence of continuous liquid electrolyte, may also be applied to other electrochemical probes, such as two-electrode probes (FIG. 6). The two-electrode configurations are often found in linear polarization resistance (LPR) probes, galvanic probes, electrochemical noise probes, electrochemical impedance spectroscopy probes, and zero-ammetry probes. Some probes may even have only one coated electrode (as shown in FIG. 7) where the auxiliary electrode (31) is not coated.

Example Test Results

Figure 8:
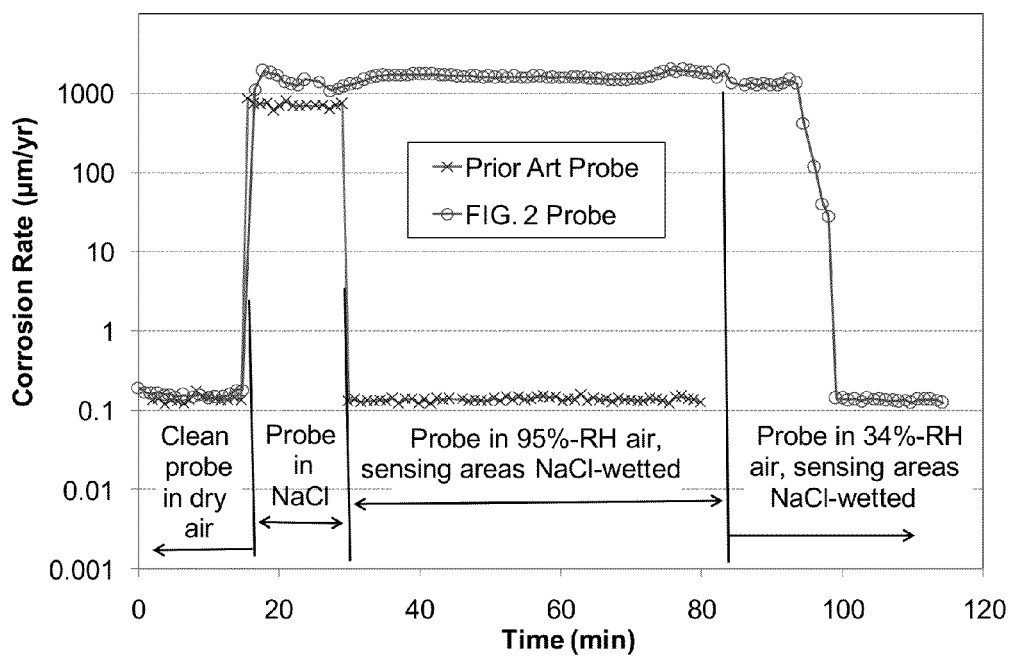
FIG. 8 illustrates the corrosion rate from a probe with fingered electrodes coated with double layers compared with the data from a prior art probe with fingered electrodes coated with a single layer.

Two CMAS probes were used in the tests for demonstrating the concept. One is a 9-electrode carbon steel probe, as shown in FIG. 2 [without the container wall (20)]. The other one is a prior art 9-electrode carbon steel probe as shown in FIG. 1 [without the container wall (20)]. The diameter of the carbon steel electrodes was 1 mm. The probe insulation (5) was epoxy. The exposed length of the coated electrodes (30) was 1" (25.4 mm). Thin PTFE tubes (about 1.5 mm OD) were used as the coating (22 and 23) for the probe electrodes. A Nafion® (Registered Trade name of Dupont) tube (diameter of 1.53 mm inside diameter and 1.80 mm outside diameter) was used as the ion conducting tubing (25). A larger-sized Nafion tube (1.83 mm ID) was used as the ion conducting material at the probe body base (27). FIG. 8 shows the results from the two probes. In dry air, both probes showed a near zero corrosion rates (0.15 µm/yr). When the probes were immersed in a 3.5% NaCl solution, the corrosion rate increased to about 700 µm/yr and 1600 µm/yr for the two probes, respectively. These corrosion rates are within the typical ranges of carbon steel localized corrosion rates in seawater or simulated seawater containing 3.5% NaCl. When the wetted probe was quickly placed in air with 95% relative humidity (RH), some of the probes' sensing areas were covered by a layer of salt solution. However, the surface of the long insulating coating (22) on the coated electrodes of the prior art probe (FIG. 1 probe) and the outside surface of the ion conducting tubing (25) did not have a continuously distributed layer of solution. The signal from the FIG. 2 probe remained the same as when it was immersed in the NaCl solution. In contrast, the prior art probe (FIG. 1 probe) decreased to 0.15 µm/yr immediately after the probe was transferred from the NaCl solution to the air with 95% RH. The fact that the corrosion signal from the FIG. 2 probe remained unchanged proved that the Nafion tube provided the ion conducting function that supports the currents flowing from one electrode to another.

The above results demonstrated that, in a wet gas or an oil-water mixture containing $H_2S$, the corrosion caused by the $H_2S$-acidified water film on the sensing surface areas can be measured by a CMAS probe with fingered electrodes coated with a ion conductive coating because the ionic coating supports the current flow from one electrode to another even though the electrodes are not immersed in a liquid electrolyte that supports the ionic flow between the sensing area of one and the sensing areas of the other electrodes.

FIG. 8 also shows that when the FIG. 2 probe was transferred from the air with 95% RH to the air with 34% RH, the corrosion rate started to decrease 10 minutes after the transfer and reached 0.15 µm/yr in another 6 minutes. The delayed decrease may be caused by the slow evaporation of the layer of salt solution on some of the probe's sensing areas because 34% RH is below the deliquescence relative humidity of NaCl and no corrosion should take place below this relative humidity. At 34% RH, the desorption of water that was already absorbed by the Nafion tube from the moisture in the air when the RH was 95% may also contribute to the delayed decrease because Nafion is not ion conductive when its water contents is low.

Other Embodiments

The electrochemical probe made of electrodes that have an insulating coating and an ion conducting coating is mainly described for use in gases or oil-water mixtures containing hydrogen sulfide that may lead the formation of corrosion products that would short-circuit the electrodes. Such probes may also be used in other environments that may cause the formation of electron conducting deposits. These environments include the engine exhaust system where carbon deposits may be formed to cause the short-circuiting.

Although the present invention has been described in details, it should be understood that various changes, substitutions, and alterations can be made hereto, without departing from the spirit and scope of the invention as defined by the appended claims.

What is claimed is:

1. An electrochemical probe for corrosion monitoring in a non-aqueous system that forms electron-conducting deposits on the probe, comprising:
   (a) a plurality of electrodes;
   (b) a body wherein a portion of each electrode is embedded to form a probe and the remaining portion of the electrodes is exposed out of the probe body;
   (c) electrical leads connected individually to each electrode at the end of the electrodes that are being embedded;
   (d) an electrical insulating coating; and
   (e) an ion conducting coating applied on the outside surface of the electrically insulating coating;
wherein the insulating coating is applied on each of the electrodes, such that all surface area of the exposed electrode—except for the electrode tip that serves as the sensing area of the electrode—is covered by the insulating coating and the electrodes are spaced such that there are gaps between the outside surfaces of the outer coatings of the adjacent electrodes near the sensing areas to prevent the formation of continuously distributed electron conducting deposits on the electrodes that may cause short-circuiting between the sensing areas of any two electrodes, while the ion conducting coating ensures the ion conducting path between the sensing areas of any two electrodes.

2. The electrochemical probe of claim 1, wherein said probe is a multielectrode probe that contains 4 or more electrodes.

3. The electrochemical probe of claim 1, wherein said insulating coating is a thin tubing.

4. The electrochemical probe of claim 1, wherein said insulating coating is epoxy.

5. The electrochemical probe of claim 1, wherein some sensing areas are larger than the other sensing areas.

6. The electrochemical probe of claim 1, wherein the exposed section of the electrodes is bent so that the distance from the sensing area of one electrode to the sensing area of any of the other electrodes is larger than when the electrodes are straight to prevent short-circuiting by a large piece of deposit that may be formed at the tip section of the probe.

7. The electrochemical probe of claim 1, wherein additional ion conducting materials are added at the probe body base to ensure the ion conducting from the ion conducting coating on one electrode to the ion conducting coatings on the other electrodes.

8. The electrochemical probe of claim 7, wherein the additional ion conducting materials are formed by porous materials after they are filled with a salt or dust that adsorbs/absorbs water or moisture.

9. The electrochemical probe of claim 1, wherein a third coating which may be non-ion conducting is applied to the outside surface of the ion conducting coating such that there are gaps between the outside surfaces of the third coating of the adjacent electrodes near the sensing areas to prevent the formation of continuously distributed electron conducting deposits on the electrodes.

10. The electrochemical probe of claim 9, wherein the outside surface of the third coating is resistant to the attachment of the electron conducting deposits so that the deposits cannot easily grow on the third coating.

11. The electrochemical probe of claim 9, wherein the third coating protects the ion conducting coating in the corrosive environments.

12. A method to form an electrochemical probe that avoids the bridging effect by electron-conducting deposits that are formed on the probe electrodes in a non-aqueous system, comprising the steps of:
   a) connecting the electrodes to metal electrical leads;
   b) embedding a portion of the electrodes at the end connected to the electrical leads in a probe body to form the probe and leave the other portion exposed; and
   c) applying an electrically insulating coating to the exposed section of a pre-selected number of electrodes, but leaving out a polished area as the sensing area at the tip of each of the selected electrodes; and
   d) applying an ion conducting coating on the outside surface of the electrically insulating coating;

wherein, the electrodes are spaced such that there are gaps between the outside surfaces of the outer coatings of the adjacent electrodes near the sensing areas to prevent the formation of continuously distributed electron conducting deposits on the electrodes, which may cause short-circuiting between the sensing area of one electrode and the sensing areas of other electrodes.

13. The method of claim 12, wherein the probe has two or three electrodes.

14. The method of claim 12, wherein the pre-selected number is 1 or more.

15. The method of claim 12, wherein the coating is epoxy.

16. The method of claim 12, wherein the coating is tubing.

17. The method of claim 12, wherein the corrosive medium contains hydrogen sulphide.

18. The method of claim 12, where in a third coating is applied on the outside surface of the ion conducting coating of the probe.

19. The electrochemical probe of claim 18, wherein the outside surface of the third coating is resistant to the attachment of the electron conducting deposits so that the deposits cannot easily grow on the outside surface of the third coating.

* * * * *